US012800372B2

(12) United States Patent
Hohlfeld et al.

(10) Patent No.: US 12,800,372 B2
(45) Date of Patent: Nov. 17, 2026

(54) SENSOR MODULE AND METHOD FOR DETERMINING AN AEROSOL DOSE RATE

(71) Applicant: Fraunhofer-Gesellschaft zur Förderung der angewandten Forschung e.V., Munich (DE)

(72) Inventors: Jens Hohlfeld, Hannover (DE); Gerhard Pohlmann, Meerbeck (DE); Olaf Holz, Hamburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 813 days.

(21) Appl. No.: 17/596,705

(22) PCT Filed: Jun. 16, 2020

(86) PCT No.: PCT/EP2020/066609
§ 371 (c)(1),
(2) Date: Dec. 16, 2021

(87) PCT Pub. No.: WO2020/254313
PCT Pub. Date: Dec. 24, 2020

(65) Prior Publication Data

US 2022/0316927 A1 Oct. 6, 2022

(30) Foreign Application Priority Data

Jun. 17, 2019 (EP) .................................... 19180566

(51) Int. Cl.
*G01F 1/74* (2006.01)
*A61M 15/00* (2006.01)
(Continued)

(52) U.S. Cl.
CPC ........... *G01F 1/74* (2013.01); *A61M 15/0065* (2013.01); *A61M 15/0083* (2014.02); *G01F 1/42* (2013.01);
(Continued)

(58) Field of Classification Search
CPC .......... A61M 15/0065; A61M 16/0003; A61M 2016/003; G01N 21/53; G01F 1/74
See application file for complete search history.

(56) References Cited

U.S. PATENT DOCUMENTS 4,370,986 A * 2/1983 Gebhart ............... A61B 5/0836 600/529
5,887,586 A * 3/1999 Dahlback .......... A61M 15/0065 128/204.22
(Continued)

FOREIGN PATENT DOCUMENTS

AT 395270 B * 11/1992
CA 2749621 A1 * 2/2012 ............... G01F 1/44
(Continued)

OTHER PUBLICATIONS

Castella AMS 950 optical sensor manual (Year: 1995).*
(Continued)

*Primary Examiner* — Kathryn E Ditmer
(74) *Attorney, Agent, or Firm* — KNOBBE, MARTENS OLSON & BEAR, LLP

(57) ABSTRACT

A method for determining an aerosol dose rate of an aerosol stream by a sensor module includes providing the aerosol stream to a patient by an inhalation device. The sensor module and the method allow an accurate determination of the aerosol dose rate actually received by the patient from the aerosol stream when using the inhalation device, the inhaled dose per breath, and the total inhaled dose per application. The sensor module can be used with existing or
(Continued)

new inhalation devices which benefit from the determination of the actually received aerosol dose rate while the patient can maintain using the familiar inhalation device.

12 Claims, 2 Drawing Sheets

(51) Int. Cl.
*G01F 1/42* (2006.01)
*G01N 21/53* (2006.01)

(52) U.S. Cl.
CPC ... *G01N 21/534* (2013.01); *A61M 2205/3313* (2013.01); *A61M 2205/3334* (2013.01)

(56) References Cited

U.S. PATENT DOCUMENTS

| | | | | | |
|---|---|---|---|---|---|
| 5,913,249 | A * | 6/1999 | Weckstrom | A61B 5/087 | 73/861.52 |
| 6,164,142 | A * | 12/2000 | Dimeff | G01F 1/42 | 600/538 |
| 6,311,568 | B1 * | 11/2001 | Kleven | G01F 1/42 | 73/861.42 |
| 7,335,164 | B2 * | 2/2008 | Mace | A61B 5/083 | 73/23.3 |
| 7,730,793 | B2 * | 6/2010 | Speldrich | G01F 1/363 | 73/861.63 |
| 2002/0033173 | A1 * | 3/2002 | Shofner, II | A61M 15/0065 | 128/200.22 |
| 2003/0016357 | A1 * | 1/2003 | Shofner | G01N 15/0211 | 356/337 |
| 2005/0045175 | A1 * | 3/2005 | McCawley | A61B 5/0813 | 128/200.14 |
| 2005/0066968 | A1 * | 3/2005 | Shofner | A61B 5/411 | 128/204.18 |
| 2009/0025718 | A1 * | 1/2009 | Denyer | A61M 15/0085 | 128/203.14 |
| 2015/0020804 | A1 * | 1/2015 | Van Der Mark | G01N 15/0211 | 128/203.14 |
| 2017/0065811 | A1 * | 3/2017 | Iwatschenko | A61M 16/16 | |
| 2017/0290527 | A1 | 10/2017 | Morisson et al. | | |
| 2017/0340844 | A1 | 11/2017 | Morisson et al. | | |

FOREIGN PATENT DOCUMENTS

| | | | | |
|---|---|---|---|---|
| CN | 105628571 | A * | 6/2016 | G01N 15/06 |
| CN | 106596364 | A * | 4/2017 | G01N 15/06 |
| IN | 2017/41002256 | A1 | 7/2018 | |
| WO | WO 2019/014373 | A1 | 1/2019 | |
| WO | WO 2020/254313 | A1 | 12/2020 | |

OTHER PUBLICATIONS

Heyder et al., Experimental Studies of the total deposition of aerosol particles in the human respiratory tract, Aerosol Science, vol. 4, Issue 3, pp. 191-208, 1973.
International Preliminary Report on Patentability mailed Dec. 30, 2021 in International Application PCT/EP2020/066609.
International Search Report & Written Opinion mailed Aug. 10, 2020 in International Application PCT/EP2020/066609.
Vecellio et al., Influence of realistic airflow rate on aerosol generation by nebulizers, International Journal of Pharmaceutics, Elsevier, vol. 371, Issues 1-2, pp. 99-105, 2009.

* cited by examiner

SENSOR MODULE AND METHOD FOR DETERMINING AN AEROSOL DOSE RATE

PRIORITY AND CROSS REFERENCE TO RELATED APPLICATIONS

This application is the U.S. National Stage Application under 35 U.S.C. § 371 of International Application No. PCT/EP2020/066609, filed Jun. 16, 2020, designating the U.S. and published in English as WO 2020/254313 A1 on Dec. 24, 2020, which claims the benefit of European Application No. EP 19180566.2, filed Jun. 17, 2019. Any and all applications for which a foreign or a domestic priority is claimed is/are identified in the Application Data Sheet filed herewith and is/are hereby incorporated by reference in their entirety under 37 C.F.R. § 1.57.

FIELD

The present invention relates to a sensor module and a method for determining an aerosol dose rate of an aerosol stream, wherein the aerosol stream is provided to a patient by an inhalation device, as well as to an inhalation device. The sensor module, the method and the inhalation device can, primarily, be used in a treatment of pulmonary or respiratory diseases.

BACKGROUND

Pulmonary or respiratory diseases, including but not limited to asthma or chronic obstructive pulmonary disease (COPD) are, typically, treated by an inhalation of drugs which are provided to a patient as liquid or solid particles in an aerosol stream by application of an inhalation device. For this purpose, a known medical inhalation device or “inhaler” having electronic aids—also denoted as a “smart inhaler”—can be used. The smart inhaler may, in particular, employ wireless transmission in order to detect a use of the inhaler by the patient, may remind the patient to take medication, and may gather data to support guide care. As a result, the smart inhaler may have a potential to improve a patient’s adherence to the prescribed therapy.

SUMMARY

The present invention relates to a sensor module and a method for determining an aerosol dose rate of an aerosol stream, wherein the aerosol stream is provided to a patient by an inhalation device, as well as to an inhalation device. The sensor module, the method and the inhalation device can, primarily, be used in a treatment of pulmonary or respiratory diseases.

DETAILED DESCRIPTION

Figure 1:
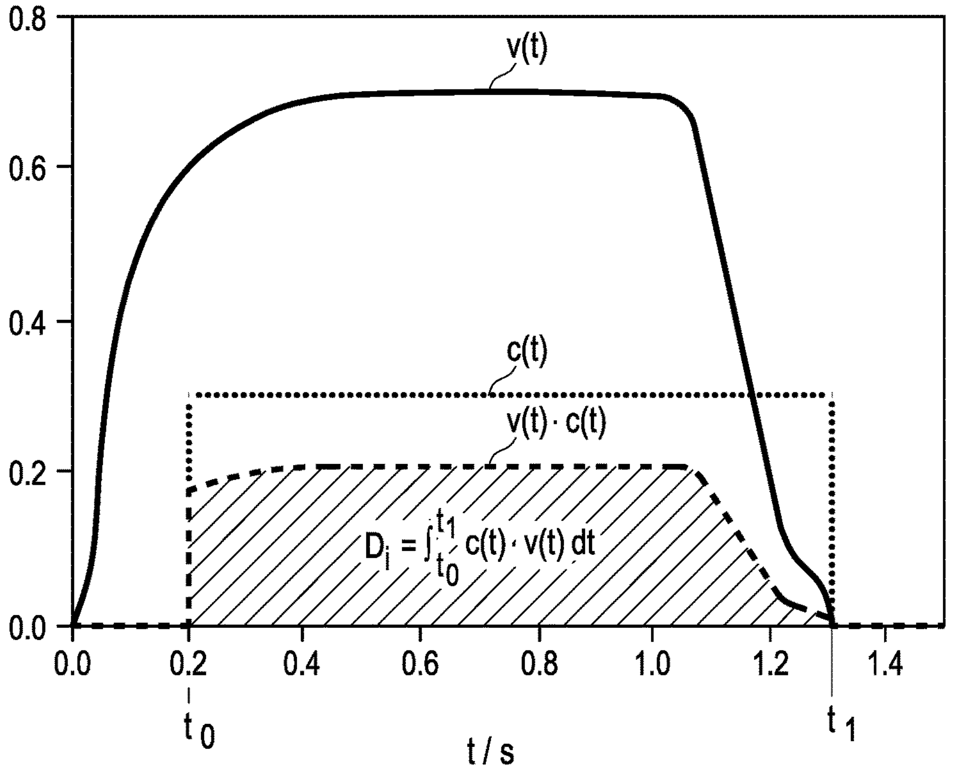
FIG. 1 schematically illustrates basic principles concerning a determination of the aerosol dose rate received by a patient from an aerosol stream in an inhalation device.

Smart inhalers, such as disclosed in US 2017/0290527 A1 or US 2017/0340844 A1, are designed not only to measure a frequency of usage by the patient but also a flow pattern, in particular an inhalation flow as described below in more detail, during the application of the smart inhaler by the patient, in particular to provide a rough estimation of an inhaled drug.

Furthermore, IN 2017/41002256 A1 discloses a smart inhaler which is capable of sensing a uniform outflow of a dose of aerosol at an outlet of the smart inhaler in order to monitor inhaling activities of the patient.

Further sensor modules and methods for determining an aerosol dose rate of an aerosol stream, wherein the aerosol stream is provided to a patient by an inhalation device, are disclosed in U.S. Pat. Nos. 4,370,986 A, 5,887,586 A, WO 2019/014373 A1, L. Vecellio et al.: “Influence of realistic airflow rate on aerosol generation by nebulizers”, Int. J. Pharma-ceutics, Elsevier, Vol. 371, No. 1-2, 17 Apr. 2009, pages 99-105, and J. Heyder et al.: “Experimental studies of the total deposition of aerosol particles in the human respiratory tract”, J. Aerosol Science, Elsevier, Vol. 4, 1 Jan. 1973, pages 191-208.

However, there is a medical need for improving patient adherence and, especially, dose accuracy, for which purpose the determination of the inhalation flow is not sufficient since it does not allow determining an aerosol dose rate actually received by the patient from the aerosol stream in the inhalation device.

It is therefore an objective of the present invention to provide a sensor module and a method for determining an aerosol dose rate of an aerosol stream, wherein the aerosol stream is provided to a patient by an inhalation device, as well as an inhalation device which at least partially avoid the above-mentioned problems.

In particular, it would be desirable that the sensor module and the corresponding method could not only determine the inhalation flow but also at least one further property of the aerosol stream as provided by the inhalation device to the patient, thereby allowing an accurate determination of the aerosol dose rate actually received by the patient from the aerosol stream when using the inhalation device.

Furthermore, it would be desirable that the sensor module could be used together with various, preferably most, existing or new inhalation devices. In this fashion it would be particularly desirable that many existing inhalation devices could, on one hand, benefit from the improved determination of the actually received aerosol dose rate while, on the other hand, the patient could maintain using the familiar inhalation device.

This problem is solved by a sensor module and a method for determining an aerosol dose rate of an aerosol stream, wherein the aerosol stream is provided to a patient by an inhalation device, as well as an inhalation device having the features of the independent claims. Preferred embodiments, which might be implemented in isolated fashion or in any arbitrary combination, are subject matter of the dependent claims.

As used in the following, the terms “have”, “comprise” or “include” or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions “A has B”, “A comprises B” and “A includes B” may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms “preferably”, “more preferably”, “particularly”, “more particularly”, “specifically”, “more specifically” or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by “in an embodiment of the invention” or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, the present invention refers to a sensor module for determining an aerosol dose rate of an aerosol stream, wherein the aerosol stream is provided to a patient by an inhalation device. As generally used, the term “aerosol” refers to an aerosolizable material that comprises solid or liquid particles of a substance which are suspended in a gas phase, wherein the particles may, in particular, be or comprise particles of a pharmaceutical preparation, such as, for example, a lung surfactant. For converting the particles into this state, an aerosolizable material, i.e. powder or a liquid solution, is treated in an “aerosol generator”, also denoted as “aerosolization device”, by vibrating meshes, ultrasonic waves or other means in order to entrain the solid or liquid particles into a gas stream of a carrier gas, such as inhaled air or a respiratory gas. In this state, the particles are, preferably, distributed across the entire volume of the carrier gas, in particular, in a uniform and finely dispersed form. As a result, the aerosol is provided as an “aerosol stream” in which the solid or liquid aerosol particles are borne and/or carried by the carrier gas stream.

As further generally used, the “aerosol dose rate” is a physical quantity referring to any one of a number, a volume, or a mass of aerosol actually received by the patient and a measurement volume. Thus, the aerosol dose rate may refer to a number, a volume, or a mass of aerosol which is delivered to the within a time interval, such as a second, a minute or an hour. However, further kinds of units may also be feasible. Further details with regard to the aerosol dose rate are provided below.

As further generally used, the term “patient” relates to a human being of any age, in particular, including children, babies, neonates and preterm neonates. Further, the term “ventilation” relates to a process of accomplishing a movement of the respiratory gases in the airways of the patient, in particular, via alternating steps of inhalation and exhalation. In contrast to normally breathing patients who are capable of performing the circulation without any additional aids, patients who are subject to respiratory support during spontaneous breathing or mechanical ventilation, require the respiratory gases at least partially to be provided from the ventilator via a ventilatory circuit. Further, the term “patient interface” relates to a unit being configured for providing a connection between the inhalation device and the respiratory track of the patient which is therefore, in general, located adjacent to the patient.

As generally used, the term “inhalation device” or simply “inhaler” refers to an apparatus which is designated for providing the aerosol stream to the patient. For this purpose, the inhalation device may comprise an aerosol generator and a patient interface for provision of the aerosol stream to the patient. In a case in which the inhalation device is provided as a smart inhaler, the inhalation device may, further, comprise electronic aids which are, particularly, designated for employing wireless transmission in order to detect a use of the inhaler by the patient, reminding the patient to take medication, and gathering data to support guide care. In addition, the inhalation device may comprise at least one sensor which is, however, directly introduced into a housing of the inhalation device and can, in general, neither be removed therefrom nor used separately outside the inhalation device.

In contrast hereto, the term “sensor module”, as used herein, refers to a device which is designed for determining at least one measureable property by using at least one sensing functionality, wherein the measureable property is related to the aerosol provided for being received by the patient. As generally used, the term “sensing functionality” refers to a fashion of acquiring the least one measureable property. Consequently, the sensor module is no inhalation device since the sensor module does not perform all functions of the inhalation device as defined above, in particular, since it neither comprises an aerosol generator nor a patient interface but concentrates on the sensing functionalities. As described below in more detail, the sensor module can, however, be attached to an inhalation device for performing the sensing functionalities in addition or as an alternative to sensing functionalities which may already be provided by sensors comprised by the inhalation device itself. In particular, the sensor module may be placed between the inhalation device and the patient, especially between the patient interface of the inhalation device and the patient.

In accordance with the present invention, the sensor module comprises:

an adaptive structure which is designed for attaching the sensor module to the inhalation device;

a measurement volume;

a concentration measurement unit which is designed for generating at least one first measurement signal depending on a concentration of the aerosol within the measurement volume;

a flow measurement unit which is designed for generating at least one second measurement signal depending on a flow of the aerosol stream through the measurement volume, wherein the flow measurement unit compromises a pressure measurement unit, wherein the pressure measurement unit comprises a differential pressure sensor, wherein a first port of the differential pressure sensor is designated for determining a first pressure in front of a flow constriction structure as comprised by the measurement volume, and wherein a second port of the differential pressure sensor is designated for determining a second pressure after the flow constriction structure, wherein the differential pressure sensor is adapted for generating the at least one second measurement signal from a difference between the first pressure and the second pressure; and an evaluation unit which is designed for determining the aerosol dose rate in the inhalation device based on a contemporaneous determination of an aerosol concentration from the at least one first measurement signal and an inhalation flow from the at least one second measurement signal.

Consequently, the sensor module according to the present invention is designated for a contemporaneous determination of the inhalation flow and the aerosol concentration of an aerosol stream in an inhalation device, thus, being able to determine the aerosol dose rate of an aerosol which is applied to a patient by using the inhalation device to which the sensor module is attached to. As described below, in particular with respect to FIG. 1, in more detail, the term "inhalation flow" v(t) refers to a flow pattern forming a breathing profile which is generated by the patient over a time interval. Further, the term "aerosol concentration" c(t) refers to an amount of aerosol which is provided over the same time interval by an aerosol generator, in particular by the aerosol generator of the inhalation device.

Based on the determination of the aerosol concentration c(t) of the aerosol stream from the at least one first measurement signal and the inhalation flow v(t) from the at least one second measurement signal, the aerosol dose rate D(t) which the patient receives at the time t is, therefore, a product being defined by Equation (1) as $$D(t)=c(t)\cdot v(t). \tag{1}$$

Integrating the aerosol dose rate D(t) over a single inhalation step from an initial time $t_0$ to a final time $t_1$, results in an inhaled dose per breath $D_i$ according to Equation (2) as $$D_i=\int_{t_0}^{t_1} c(t)\cdot v(t)dt \tag{2}$$

After having taken the n-th breath through the inhalation device, the total inhaled dose D per application is in accordance with Equation (3)

$$D=\sum\nolimits_{i=0}^{n} D_i \tag{3}$$

As a result, the total inhaled dose D can be accurately determined if both the inhalation flow v(t) and the aerosol concentration c(t) are measured during each inhalation step i=0 . . . n in a contemporaneous fashion. As generally used, the term "contemporaneous" relates to measuring the first measurement signals and the second measurement signals within the same time interval $[t_0, t_1]$ in a manner that the first measurement signals and the second measurement signals are applicable for the same time interval for being used in determining the product according to Equation (1).

In accordance with the present invention, the sensor module comprises at least one measurement volume. As generally used, the "measurement volume" refers to a spatial area which is designated for allowing the aerosol stream passing through for determining a measurable quantity of the aerosol. Specifically, the measurement volume is designed for measuring both a concentration of the aerosol within the measurement volume and a flow of the aerosol over the measurement volume. For this purpose, the measurement volume may comprise a single section or, preferentially, at least two different sections which may, especially, be designed for a particular sensing functionality, preferably a first section being adapted for measuring the concentration of the aerosol and a second section for measuring the flow of the aerosol. However, other arrangements of the measurement volume may also be conceivable.

In a particularly preferred embodiment, the measurement volume may, in particular, be or comprise a spatial area which may be delimited by a circumference along an internal surface of the sensor module which may, thus, form a surface of the measurement volume. In this embodiment, the sensor module may comprise at least one housing, wherein the housing may be designed for providing mechanical stability to the sensor module in a fashion that the sensor module can be easy handled by a user, such as by the patient or by medical personnel. Herein, the surface of the measurement volume may, particularly, be streamlined with respect to the flow of the aerosol stream. For this purpose, the measurement volume may, preferably, have a coaxial symmetry with respect to a direction of the flow of the aerosol stream. However, other forms of the measurement volume may still be possible. Herein, the surface of the first section of the measurement volume may comprise walls which may be smooth and free of edges, recesses and protrusions as far as possible for measuring the concentration of the aerosol with as little influence by form and arrangement of the surface as possible while the second section of the measurement volume may comprise a flow constriction structure as described below in more detail. This kind of arrangement may, on one hand, provide accurate measurement results and, on the other hand, avoid that aerosol may be deposited on the walls of the measurement volume, particularly, in order to avoid an undesired staining of the surfaces of the measurement volume.

Further according to the present invention, the sensor module comprises a concentration measurement unit which is designed for generating at least one first measurement signal depending on a concentration of the aerosol within the measurement volume. As already indicated above, the term "aerosol concentration", abbreviate to c(t), refers to the amount of aerosol as a number per volume or, preferably, a mass per volume which passes the measurement volume during a selected time interval. In general, measuring the aerosol concentration may be performed in any suitable fashion, wherein, however, employing an interaction of the aerosol with incident light may, especially, be preferred here. As generally used, the term "interaction" refers to an encounter of the aerosol with the incident light, by which action the incident light may be altered in a fashion that it experiences an alteration being in relationship with at least one physical property of the aerosol having an encounter with the incident light when passing through the measurement volume. As a result, the alteration of the incident light following this encounter with the aerosol passing through the measurement volume is capable of allowing a determination of a physical property of the aerosol provided that the relationship between the alteration of the incident light and the physical property of the aerosol particles is known.

For this purpose, at least one optical measurement unit is used as the concentration measurement unit, wherein the optical measurement unit is designed for generating a first measurement signal which depends here on the interaction of the incident light with the aerosol passing the measurement volume. As used herein, the "optical measurement unit" refers to a device having at least one light detecting element which is designated for generating a first measurement signal by surveilling the alteration of the incident light, thus, as described above, allowing the determination of the physical property of the aerosol. As generally used, the terms "optical" and "light" refer to electromagnetic radiation in the visible spectral range which may also include the adjacent infrared spectral range and ultraviolet spectral range. Referring to ISO standard ISO-21348 in a version applicable at the date of application of this document, the "visible spectral range" generally relates to a wavelength of 380 nm to 760 nm, whereas the "infrared spectral range"

generally refers to a wavelength of 760 nm to 1000 μm, wherein the wavelength of 760 nm to 1.4 μm is usually denoted as "near infrared spectral range", and whereas the "ultraviolet spectral range" refers to a wavelength of 1 nm to 380 nm, preferably of 100 nm to 380 nm. Preferably, the light used in connection with the present invention is light selected from the visible or the near infrared spectral range.

Herein, the alteration of the light beam may be a scattering or an extinction of the incident light in the measurement volume upon the passing of the aerosol. As generally used, the term "scattering" refers to an alteration of a direction of the incident light upon passing of the aerosol through he measurement volume while the term "extinction" relates to an attenuation of the light following the encounter of the light with the aerosol within the measurement volume. Thus, a grade of the scattering or the extinction of the light results in the first measurement signal that may be used as the first measurement signal which depends on the concentration of the aerosol within a measurement volume for determining the desired concentration measurement of the aerosol. Alternatively or in addition, other kinds of alterations of the light beam may be measured, such an alteration of a a diffraction, a reflection, a refraction, or a polarization of the incident light.

The light which may be used for the interaction with the aerosol within the measurement volume may be provided by at least one light source comprised by the optical measurement unit, wherein the light source is designated to emit the desired light for this purpose. Herein, the light source can be selected from at least one of: a laser, in particular a laser diode, although in principle, alternatively or additionally, other types of lasers can also be used; a light emitting diode; an organic light source, in particular an organic light emitting diode; a structured light source. Alternatively or additionally, other light sources may also be feasible. In a particular embodiment, the light source may be an extended light source, a extension of which can be designed for fitting to a cross-section of the measurement volume. Preferably, the extended light source may be provided in form of a light emitting ring which may be adapted to a preferred coaxial symmetry of the measurement volume with respect to a direction of the flow of the aerosol stream as described elsewhere herein. In addition, further types and arrangements of the light sources may also be feasible.

The alteration of the incident light, such as the scattered light or the light extinction, can be measured by at least one light detecting element as further comprised by the optical measurement unit. In a preferred embodiment, one or more light detecting elements can be placed at various locations for measuring the light scattering. In a further preferred embodiment, one or more light detecting elements may be located in an opposite manner with respect to the light source such that the aerosol can pass between the light source and the light detecting element, thereby being capable of measuring the light extinction being caused by the passing aerosol. In the particular embodiment in which the light source may be an extended light source, also the light detecting element may exhibit an extension which can be designed for fitting to a cross-section of the light source. Preferably, the light detecting element may, thus, be a light detector ring which may arranged symmetrically with respect to the extended light source, such as provided in form of the light emitting ring, wherein the light detector ring may, in particular, be placed in a constant distance from the light emitting ring. However, further kinds of number and arrangements of the light detecting elements may also be conceivable.

Further according to the present invention, the sensor module comprises at least one flow measurement unit which is designed for generating at least one second measurement signal which depends on a flow of the aerosol stream through the measurement volume. In a particularly preferred embodiment, a total flow which is averaged over the measurement volume, preferably the measurement volume which has a coaxial symmetry with respect to a direction of the flow of the aerosol stream, can be measured by observing a pressure drop along the circumference of the internal surface of the sensor module forming the surface of the measurement volume, in particular, along a flow constriction structure, in particular an aperture, using a pressure sensor which generates a second measurement signal. Such an arrangement can be considered as a pressure measurement unit, specifically a so-called "Prantl probe" or "Pitot probe".

Thus, as further described in the examples below, a differential pressure sensor is used as the pressure measurement unit, wherein the term "differential pressure sensor" refers to a particular kind of pressure sensor having two individual ports, usually denoted as "p+ pressure port" and "p− pressure port", between which a difference in pressure can be measured. For this purpose, a first multitude of holes along the circumference of the surface of the measurement volume in front of the flow constriction structure is in pressure connection with a first pressure measurement chamber, wherein the first pressure measurement chamber itself may be in connection with the p+ pressure port of the differential pressure sensor, whereby a first pressure in front of the flow constriction structure is measured. Similarly, a second multitude of holes along the circumference of the surface of the measurement volume after the flow constriction structure is in pressure connection with a second pressure measurement chamber being itself in connection with the p− pressure port of the differential pressure sensor, whereby a second pressure after the flow constriction structure is measured. Herein, the terms "in front of" and "after" with respect to the flow constriction structure are considered with regard to the direction of the aerosol stream. However, further kinds and arrangements of the pressure sensor can also be conceived.

Further according to the present invention, the sensor module comprises at least one evaluation unit which is designed for determining desired items of information, i.e. the aerosol dose rate D(t) in the inhalation device based on the contemporaneous determination of the aerosol concentration c(t) of the aerosol stream from the at least one first measurement signal and an inhalation flow v(t) from the at least one second measurement signal. As generally used, the term "evaluation unit" refers to a device which is designed for generating the desired items of information as indicated above. For this purpose, the evaluation unit may be or may comprise one or more integrated circuits, such as one or more application-specific integrated circuits (ASICs), and/or one or more data processing devices, such as one or more computers, preferably one or more microcomputers and/or microcontrollers. Additional components may be comprised, such as one or more preprocessing devices and/or data acquisition devices, such as one or more devices for receiving and/or preprocessing of the sensor signals, such as one or more AD-converters and/or one or more filters. Herein, the evaluation unit may be provided as a single component or may, preferably, comprise at least two separate components, wherein at least one component may, fully or partially, be integrated into an electronic device, in particular an electronic communication unit, such as a smartphone or a tablet. However, further kinds of evaluation units or electronic devices may also be conceivable.

Further, the evaluation unit may comprise one or more data storage devices. Further, as outlined above, the evaluation unit may comprise one or more interfaces, such as one or more wireless interfaces or, preferably, one or more wire-bound interfaces, wherein the interfaces may communicate between the optical measurement unit and the evaluation unit, on one hand, and the flow measurement unit and the evaluation unit, on the other hand. In addition, the evaluation unit of the present invention may, especially, be designated to further communicate with the electronic aids of the inhalation device being a smart inhaler, preferably, by one or more wireless interfaces, preferably one or more Bluetooth modules. As a result of this communication with the electronic aids of the inhalation device, the smart inhaler can be configured for using the items of information as provided by the evaluation unit of the sensor module for detecting a proper use of the inhaler by the patient, and for gathering additional data to support guide care. As a result, the smart inhaler equipped with the sensor module according to the present invention may have a potential to further improve the patient's adherence to the prescribed therapy.

The evaluation unit can, in addition, be designed to perform the method for determining at least one of the aerosol dose rate D(t) received by the patient from the aerosol stream in the inhalation device, the inhaled dose per breath $D_i$, and the total inhaled dose D per application as defined above in more detail. For this purpose, the evaluation unit may be adapted to perform at least one computer program, in particular by implementing any one or all of the methods steps as described herein. As an example, one or more algorithms may be implemented which, by using the optical measurement signals as input variables, may determine the desired items of information.

In particular, the evaluation unit may, especially, be designed for converting the first measurement signal into the desired information about the aerosol concentration c(t). This kind of conversion may, preferably, be nearly exact in a preferred embodiment in which a relationship between the aerosol concentration c(t) of the aerosol stream through the measurement volume and an intensity of the alteration of the incident light, such as the scattered light or the light extinction, by the aerosol within the measurement volume has been established by calibration measurements, preferably prior to the optical measurements as performed here, for a particular type of inhalation device. However, in case a lower accuracy of the measured aerosol concentration c(t) may be acceptable, an average calibration function can also be used. Still, a high and identically repeatability can be achieved in both cases.

Similarly, the evaluation unit may, especially, be designed for converting the second measurement signal into the desired information about the inhalation flow v(t). Specifically, by knowing a relationship between the pressure drop as, preferably, measured by the differential pressure sensor as described elsewhere herein in more detail, and the flow of the aerosol through the measurement volume, such as comprised by a specific calibration function for the sensor module, the inhalation flow v(t) can be determined from the measured pressure drop.

Further according to the present invention, the sensor module comprises an adaptive structure which is designed for attaching the sensor module to the inhalation device for providing the aerosol stream to the patient. In a particularly preferred embodiment, the adaptive structure may be designed for placing the sensor module between the inhalation device and the patient, especially between the patient interface of the inhalation device and the patient. As used herein, the term "adaptive structure" relates to a section of the sensor module which allows attaching, preferably tightly attaching, the sensor module of the present invention to various, preferably most, existing or new inhalation devices, in a fashion that the sensor module could complement potentially existing sensing functionalities which may already be provided by sensors comprised by the inhalation device itself. As a result, many existing inhalation devices could, on one hand, benefit from the improved determination of the actually received aerosol dose rate D(t), the inhaled dose per breath $D_i$ and/or the total inhaled dose D per application, all of which can be measured by the sensor module according to the present invention while, on the other hand, the patient could maintain using the familiar inhalation device.

In order to be able to suitable for as many existing inhalation devices as possible, the adaptive structure may, preferably, assume a form which could be attached to most existing inhalation devices. Since most existing inhalation devices, preferably, have a coaxial symmetry with respect to a direction of the flow of the aerosol stream, the adaptive structure may, thus, preferably also exhibit the coaxial symmetry with respect to a direction of the flow of the aerosol stream. In a particularly preferred embodiment, the adaptive structure may, therefore, be provided in form of an adapter ring which may follow the housing of the sensor module exhibiting the coaxial symmetry. As a result, the adapter ring can, thus, be attached to a housing or a tubing being present at an extension of the inhalation device also exhibiting the coaxial symmetry. Further, the adapter ring could comprise a conical form, thus, allowing the adapter ring to be attached to tubings of different diameter, whereby a range of applicability of the sensor module of the present invention can further be increased. In addition, although generally not required, the adaptive structure could also comprise one or more recesses or protrusions which could be adapted for securing the adaptive structure to the housing or the tubing of the inhalation device where the adaptive structure is attached to.

In a further aspect, the present invention refers to an inhalation device for providing an aerosol stream to a patient. For this purpose, the inhalation device comprises an aerosol generator and a patent interface for provision to the patient and is, further, equipped with a sensor module for determining an aerosol dose rate of an aerosol stream as described herein elsewhere. In a case in which the inhalation device is a smart inhaler, the inhalation device may, further, comprise electronic aids which are, particularly, designated for employing wireless transmission for various purposes. In addition, the inhalation device may comprise at least one sensor which is, however, directly introduced into a housing of the inhalation device and can, in general, neither be removed therefrom nor used separately outside the inhalation device. For further details with respect to the inhalation device, reference may be made to the description of the sensor module, the exemplary embodiments thereof and the method as described herein.

In a further aspect, the present invention refers to a method for determining an aerosol dose rate received by a patient from an aerosol stream in an inhalation device, wherein the inhalation device is designated for providing the aerosol stream to the patient. As used herein, this method comprises the following steps:

attaching a sensor module to an inhalation device, wherein the inhalation device is designed for providing the aerosol stream to a patient;

generating at least one first measurement signal depending on a concentration of the aerosol within a measurement volume comprised by the sensor module;

generating at least one second measurement signal depending on a flow of the aerosol stream through the measurement volume; and determining the aerosol dose rate D(t) in the inhalation device based on a contemporaneous determination of an aerosol concentration c(t) from the at least one first measurement signal and an inhalation flow v(t) from the at least one second measurement signal.

Herein, the indicated steps may be performed in the given order, wherein, preferably, any or all of the indicated steps may be preformed at least partially concurrently. Further method steps, whether described in this document, such as the following optional steps, or not, may, additionally, be performed.

In addition, the following optional method step can be performed after determining the aerosol dose rate D(t) in the inhalation device as indicated above:

determining an inhaled dose per breath $D_i$ by integrating the aerosol dose rate D(t) over a single inhalation step from an initial time $t_0$ to a final time $t_1$.

In addition, the further following optional method step can also be performed after the preceding step of determining the inhaled dose per breath $D_i$:

determining a total inhaled dose D per application after having taken the n-th breath through the inhalation device by summing the inhaled doses per breath $D_i$.

Herein, the evaluation device may, preferably, further be adapted for determining the inhaled dose per breath $D_i$ and the total inhaled dose D per application after having taken the n-th breath through the inhalation device.

In a further aspect, the present invention refers to a computer program product which comprises executable instructions for performing any or all of the method steps as described elsewhere herein.

For further details with respect to the method or to the computer program product, reference may be made to the description of the sensor module and of the exemplary embodiments thereof elsewhere in this document.

Consequently, the sensor module and the method according to the present invention may, thus, not only allow determining the inhalation flow v(t) but also the aerosol concentration c(t) as at least one further property of the aerosol stream being provided by the inhalation device to the patient. As a result thereof, the sensor module and the corresponding method allow an accurate determination of the aerosol dose rate D(t) which has been actually received by the patient from the aerosol stream when using the inhalation device, the inhaled dose per breath $D_i$ and the total inhaled dose D per application as further defined above. Herein, the sensor module can be used together with various, preferably most, existing or new inhalation devices. As a result thereof, many existing inhalation devices may, on one hand, benefit from the improved determination of the actually received aerosol dose rate while, on the other hand, the patient can maintain using the familiar inhalation device.

Further optional features and embodiments of the invention are disclosed in more detail in the subsequent description of preferred embodiments, preferably in conjunction with the dependent claims. Therein, the respective optional features may be implemented in an isolated fashion as well as in any arbitrary feasible combination, as the skilled person realizes. It is emphasized that the scope of the invention may not be restricted by the preferred embodiments. The embodiments are schematically depicted in the Figures. Herein, identical reference numbers refer to identical or functionally comparable elements.

In order to better understand the functioning of a sensor module 110 for determining an aerosol dose rate D(t) received by a patient from an aerosol stream 112 in an inhalation device, FIG. 1 schematically illustrates the basic principals concerning the determination of the aerosol dose rate D(t).

According to the present invention, the sensor module 110 is designed for determining the aerosol dose rate D(t) actually received by the patient from the aerosol stream 112 in an inhalation device based on a contemporaneous determination of aerosol concentration c(t) of the aerosol stream 112 from first measurement signals and of an inhalation flow v(t) from second measurement signals, wherein the first measurement signals depend on a concentration of the aerosol within a measurement volume 114 while the second measurement signals depend on a pressure drop of the aerosol over the measurement volume 114.

FIG. 1 schematically depicts, as a full line, a temporal course of a breathing profile in arbitrary units which corresponds to the inhalation flow v(t) as generated by the patient over a time t in seconds within the inhalation device. Further, FIG. 1 schematically shows, as a dotted line, the temporal course of the aerosol concentration c(t) in arbitrary units which corresponds to an amount of the aerosol being provided at the same time t in seconds by an aerosol generator of the inhalation device.

Further, FIG. 1 schematically depicts, as a dashed line, the temporal course of the aerosol dose rate D(t) in arbitrary units being received by the patient at the time t which is defined as a product of the aerosol concentration c(t) of the aerosol stream 112 and of the inhalation flow v(t) by Equation (1) as $$D(t)=c(t)\cdot v(t). \tag{1}$$

Further, FIG. 1 schematically illustrates, as a hatched area under the temporal course of the aerosol dose rate D(t), an inhaled dose per breath $D_i$ according to Equation (2) as $$D_i=\int_{t_0}^{t_1} c(t)\cdot v(t)dt \tag{2}$$

in arbitrary units, which is obtained by integrating the aerosol dose rate D(t) over a single inhalation step from an initial time $t_0$ to a final time $t_1$.

After having taken the n-th breath through the inhalation device, a total inhaled dose D per application can be determined according to Equation (3) by $$D=\sum_{i=0}^{n} D_i \tag{3}$$

(not depicted here). Thus, the total inhaled dose D can be accurately determined if both the inhalation flow v(t) and the aerosol concentration c(t) are measured during each inhalation step i=0 . . . n in a contemporaneous fashion.

Figure 2:
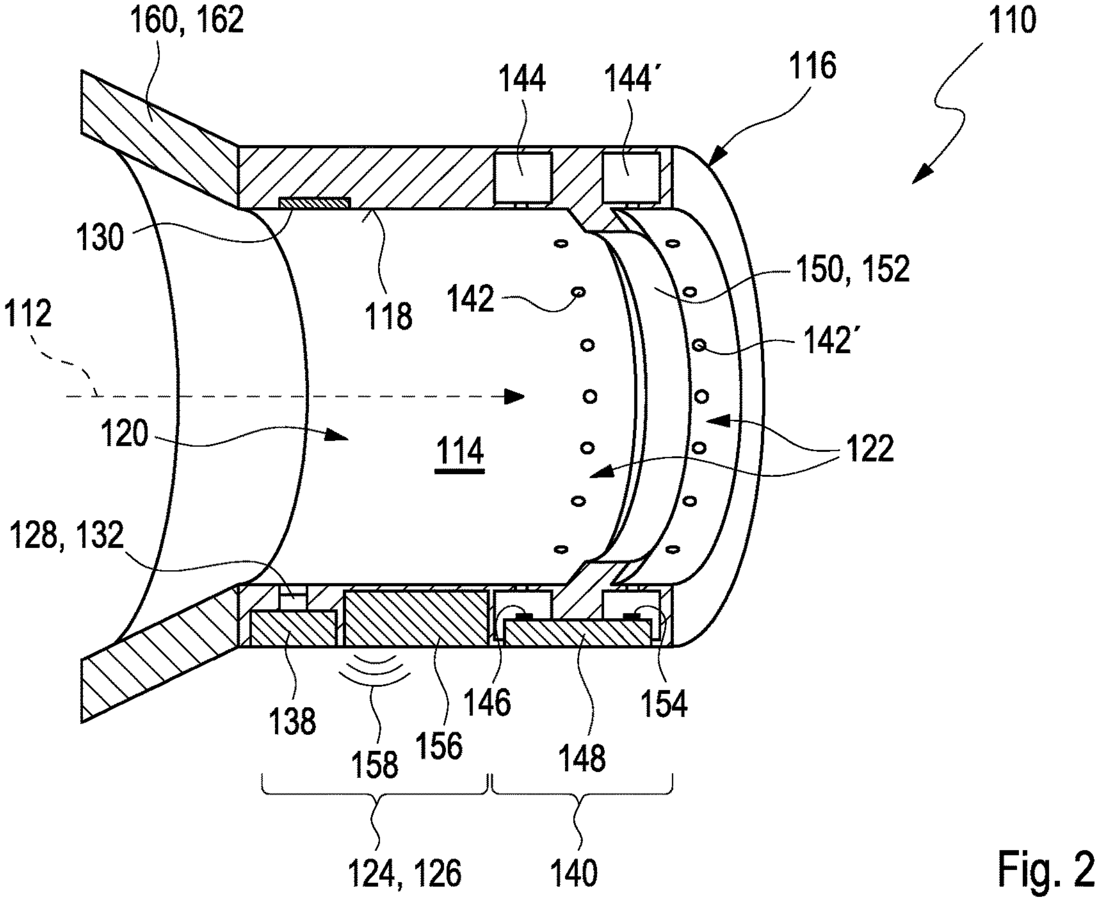
FIG. 2 illustrates a preferred embodiment of a sensor module for determining the aerosol dose rate in a sectional view.

FIG. 2 schematically illustrates a preferred embodiment of the sensor module 110 for determining the aerosol dose rate D(t) and, optionally, the inhaled dose per breath $D_i$ and the total inhaled dose D being received by the patient from the aerosol stream 112 as provided by the inhalation device.

In this embodiment, the sensor module 110 comprises at least one housing 116 which may be, especially be designed for providing mechanical stability to the sensor module 110, thus, allowing easy handling of the sensor module 110 by a user, such as the patient or medical personnel. As illustrated here, the housing 116 may delimit an internal surface 118 of the sensor module 110, wherein the internal surface 118 may constitute a spatial area for the measurement volume 114 of the sensor module 110. Herein, the internal surface 118 which, thus, forms a surface of the measurement volume 114 may, in particular, be streamlined with respect to the flow of the aerosol stream 112. As depicted in FIG. 2, both the housing 116 and the measurement volume 114 may have a coaxial symmetry with respect to the direction of the flow of the aerosol stream 112. In addition, the internal surface 118 may comprise walls having which may be smooth and free of edges, recesses and protrusions as far as possible. As a result, the flow of the aerosol stream 112 may, thus, be capable of passing the measurement volume 114 with as little influence as possible. This kind of arrangement may, on one hand, provide accurate measurement results and, on the other hand, avoid that aerosol may be deposited on the internal surface 118. Thus, the aerosol stream 112 passes through the measurement volume 114 in which both the aerosol concentration c(t) and a pressure drop of the aerosol are measured. For this purpose, the measurement volume 114 may comprise a first section 120 in which the aerosol concentration c(t) may be measured and a second section 122 in which the pressure drop of the aerosol may be measured.

Thus, as shown in FIG. 2, a concentration measurement unit 124 which is designed for generating the first measurement signals depending on a concentration of the aerosol within the measurement volume 114 is located at the first section 120 of the measurement volume 114. In the embodiment of FIG. 2, the concentration measurement unit 124 is provided as in form of an optical measurement unit 126 which comprises a light source 128 and a light detecting element 130. As schematically depicted here the light source 128 may be a laser diode or a light emitting diode 132 which may located at the internal surface 118 of the housing 116 adjoining the measurement volume 114 and which may emit light of the least one desired wavelength into the measurement volume 114, wherein the passing aerosol stream 112 may alternate the emitted light, in particular, by scattering the light or by absorbing a partition of the light, wherein for a particular aerosol, the intensity of the scattered light or of the transmitted light may be proportional to the aerosol concentration c(t). The light detecting element 130 which may be or comprise a photosensitive semiconductor element may be located at an opposite position with respect to the light source 128, thus, allowing the aerosol stream 112 to pass between the light source 128 and the light detecting element 130.

Figure 3:
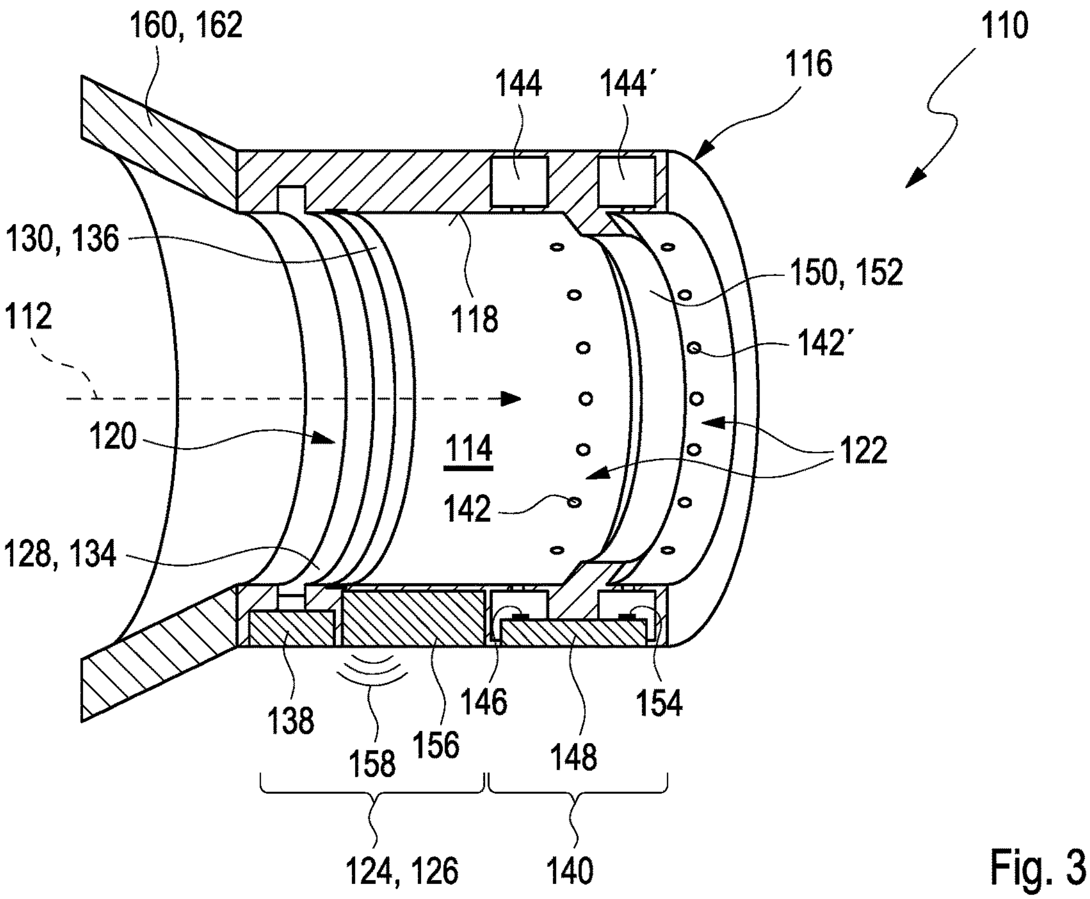
FIG. 3 illustrates a further preferred embodiment of the sensor module for determining the aerosol dose rate in a sectional view.

A further preferred embodiment of the optical measurement unit 126 is schematically illustrated in FIG. 3. Herein, the light source 128 is designed as a light emitting ring 134 whereas the light detecting element 130 is designed as a light detecting ring 136. Herein, the light emitting ring 134 may comprise a plurality of light emitting diodes which are arranged following each other along the ring. Similarly, the light detecting ring 136 may comprise a plurality of photosensitive semiconductor elements following each other along the ring. In this particular embodiment, the light emitting ring 134 and the light detecting ring 136 may, preferably, be arranged in a concentric manner with respect to each other, thereby maintaining the preferred coaxial symmetry of the measurement volume 114 with respect to a direction of the aerosol stream 112. As an advantage of this embodiment, the emitted light can illuminate the first section 120 of the measurement volume 114 in a significantly improved fashion compared to the embodiment as shown in FIG. 2. Further, this advantage is increased by the light detecting ring 136 which allows a detection considerably more distributed over the measurement volume 114, whereby a more accurate detection of the aerosol concentration c(t) within the spatial area of the first section 120 of the measurement volume 114 may obtained.

As depicted further in FIGS. 2 and 3, the optical measurement unit 126 comprises aerosol detector electronics 138 which is designed for triggering the light source 128, such as the light emitting diode 132 of FIG. 2 or the light emitting ring 134 of FIG. 3, and for generating the first measurement signals which depends on aerosol concentration c(t) within the first section 120 of the measurement volume 114.

As illustrated in FIGS. 2 and 3, the sensor module 110 further comprises a pressure measurement unit 140 which is designed for generating the second measurement signals depending on a pressure drop of the aerosol over the measurement volume 114. In the depicted embodiment, a first multitude of holes 142 along a circumference of the internal surface 118 of the housing 116 adjoining the second section 122 of the measurement volume 114 are in pressure connection with a pressure measurement chamber 144 which is itself in connection with a p+ pressure port 146 of a differential pressure sensor 148. As a result, a first pressure which prevails in front of an aperture 150 functioning as a flow constriction structure 152 is measured. In addition hereto, a second pressure is measured after the aperture 150, wherein a second multitude of holes 142' along the circumference of the internal surface 118 of the housing 116 also adjoining the second section 122 of the measurement volume 114 are in pressure connection with a further pressure measurement chamber 144' which is itself in connection with a p− pressure port 154 of the differential pressure sensor 148. Hereby, a second pressure which prevails after the aperture 150 which functions as the flow constriction structure 152 is measured. Further, the differential pressure sensor 148 is designed for measuring a pressure drop by determining a difference between the first pressure and the second pressure. Further, by knowing a relationship between the pressure drop and the flow of the aerosol stream 112 through the measurement volume 114, such as by using a specific calibration function, the inhalation flow v(t) can be determined from the pressure drop as measured in this fashion. However, further procedures for determining the inhalation flow v(t) are also conceivable.

As illustrated in FIGS. 2 and 3, the sensor module 110 further comprises an evaluation unit 156 which is designed for determining the aerosol dose rate D(t) in the inhalation device based on the contemporaneous determination of the aerosol concentration c(t) of the aerosol stream 112 from the first measurement signals and the inhalation flow v(t) from the second measurement signals as desired items of information. As schematically depicted here, the evaluation unit 156 may be formed as a separate evaluation unit 156 independent from the optical measurement unit 126 and the differential pressure sensor 148 but may, preferably, be connected to both the optical measurement unit 126 and the differential pressure sensor 148, such as by suing wire-bound leads (not depicted here) or a wire-less connection in order to receive the corresponding first and second measurement signals. Alternatively (not depicted here), the evaluation unit 154 may constitute a combined unit together with the optical measurement unit 126 and/or the differential pressure sensor 148. As further depicted here, a Bluetooth interface 158 may be used for forwarding the determined items of information to a receiving unit (not depicted here) comprised by the inhalation unit. However, other kinds of interfaces may also be feasible.

In addition, the sensor module 110 further comprises an adaptive structure 160 which is designed for attaching the sensor module 110 to the inhalation device for providing the aerosol stream 112 to the patient. As illustrated in FIGS. 2 and 3, the adaptive structure 160 is provided as an adapter ring 162 which may follow the housing 116 of the sensor module 110 by exhibiting the coaxial symmetry. Thus, the adapter ring 162 can be attached to a housing or a tubing at an extension of the inhalation device (not depicted here) which may also exhibit the coaxial symmetry. As further illustrated here, the adapter ring 162 could comprise a conical form such that the adapter ring 162 may be attached to tubings of different diameter. However, further kinds and arrangements of the adaptive structure 160 may also be feasible. As a result thereof, the sensor module 110 can be used together with various existing or new inhalation devices. Thus, many existing inhalation devices may, on one hand, benefit from the improved determination of the aerosol dose rate D(t) while, on the other hand, the patient can maintain using the familiar inhalation device.

Figure 4:
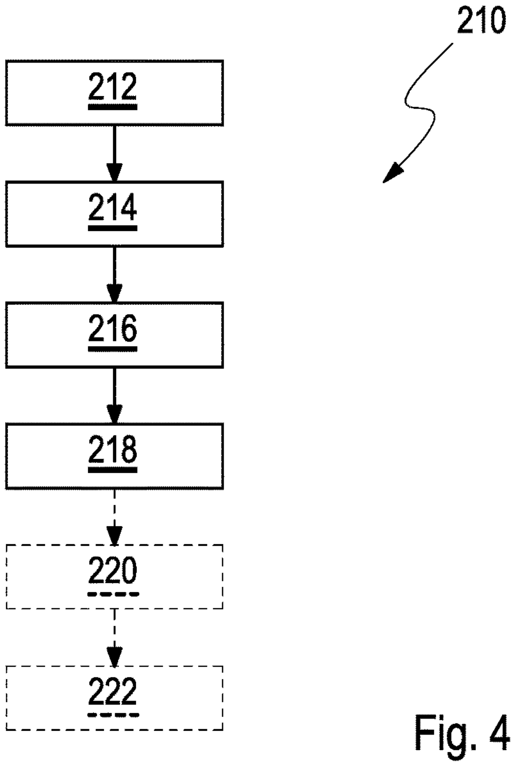
FIG. 4 schematically illustrates a preferred embodiment of a method for determining the aerosol dose rate.

FIG. 4 schematically illustrates a preferred embodiment of a method 210 for determining an aerosol dose rate D(t) received by a patient from the aerosol stream 112 in the inhalation device, wherein the inhalation device is designated for providing the aerosol stream 112 to the patient.

In an attaching step 212 the sensor module 110 is attached to the inhalation device for providing the aerosol stream 112 to the patient by using an adaptive structure 160.

In a concentration measuring step 214, the first measurement signals which depend on the aerosol concentration c(t) within the measurement volume 114 are generated by using the concentration measurement unit 124.

In a pressure measuring step 216, the second measurement signals which depend on the pressure drop of the aerosol over the measurement volume 114 are generated by using the pressure measurement unit 140.

In a determining step 218, the aerosol dose rate D(t) in the inhalation device is determined based on the contemporaneous determination of the aerosol concentration c(t) of the aerosol stream 112 from the first measurement signals and of the inhalation flow v(t) from the second measurement signals by using the evaluation unit 156.

In a further optional determining step 220, the inhaled dose per breath $D_i$ is determined by integrating the aerosol dose rate D(t) over a single inhalation step from an initial time $t_0$ to a final time $t_1$ by using the evaluation unit 156 again.

In a further optional determining step 222, the total inhaled dose D per application after having taken the n-th breath through the inhalation device by the patient is determined by summing the inhaled doses per breath $D_i$, thereby again using the evaluation unit 156.

Consequently, the method 210 not only allows determining the inhalation flow v(t) but also the aerosol concentration c(t), whereby an accurate determination of the aerosol dose rate D(t) actually received by the patient from the aerosol stream 112 when using the inhalation device, the inhaled dose per breath $D_i$ and the total inhaled dose D per application can be achieved.

LIST OF REFERENCE NUMBERS

110 sensor module
112 aerosol stream
114 measurement volume
116 housing
118 internal surface
120 first section
122 second section
124 concentration measurement unit
126 optical measurement unit
128 light source
130 light detecting element
132 light emitting diode
134 light emitting ring
136 light detecting ring
138 aerosol detector electronics
140 pressure measurement unit
142, 142' hole
144, 144' pressure measurement chamber
146 p+ pressure port
148 differential pressure sensor
150 aperture
152 flow constriction structure
154 p− pressure port
156 evaluation unit
158 Bluetooth interface
160 adaptive structure
162 adapter ring
210 method
212 attaching step
214 concentration measuring step
216 pressure measuring step
218 determining step
220 determining step

What is claimed is:

1. A sensor module for determining an aerosol dose rate of an aerosol stream, wherein the aerosol stream is provided to a patient by an inhalation device, wherein the sensor module comprises:

an adaptive structure configured to attach the sensor module to the inhalation device;

a measurement volume;

a concentration measurement unit configured to generate at least one first measurement signal depending on a concentration of the aerosol stream within the measurement volume;

a flow measurement unit configured to generate at least one second measurement signal depending on a flow of the aerosol stream through the measurement volume, wherein the flow measurement unit compromises a pressure measurement unit, wherein the pressure measurement unit comprises a differential pressure sensor, wherein a first port of the differential pressure sensor is configured for determining a first pressure in front of a flow constriction structure comprised within the measurement volume, and wherein a second port of the differential pressure sensor is configured for determining a second pressure after the flow constriction structure, wherein the differential pressure sensor is configured for generating the at least one second measurement signal from a difference between the first pressure and the second pressure; and an evaluation unit configured to determine the aerosol dose rate in the inhalation device based on a contemporaneous determination of an aerosol concentration from the at least one first measurement signal and an inhalation flow from the at least one second measurement signal, wherein the concentration measurement unit comprises an optical measurement unit, wherein the optical measurement unit is configured to generate the at least one first measurement signal depending on an interaction of light with the aerosol stream within the measurement volume, wherein the optical measurement unit comprises at least one light source and at least one light detecting element, wherein the light source is a light emitting ring, and wherein the light detecting element is a light detecting ring.

2. The sensor module of claim 1, wherein the light emitting ring and the light detecting ring are arranged in a coaxial manner with respect to each other.

3. The sensor module of claim 1, wherein the light emitting ring is shaped to extend around a cross-section of the measurement volume.

4. The sensor module of claim 1, wherein the light detecting ring is shaped to extend around a cross-section of the light emitting ring.

5. The sensor module of claim 1, wherein the measurement volume is or comprises a spatial area delimited by a circumference along an internal surface of the sensor module.

6. The sensor module of claim 1, wherein the adaptive structure is an adaptor ring configured to tightly attachable to the inhalation device.

7. The sensor module of claim 1, wherein a first multitude of holes is provided along a circumference of the measurement volume in front of the flow constriction structure, wherein a second multitude of holes is provided along the circumference of the measurement volume after the flow constriction structure, wherein each multitude of holes is in fluid connection to a corresponding pressure measurement chamber, wherein each pressure measurement chamber is in fluid connection to a corresponding port of the differential pressure sensor.

8. The sensor module of claim 1, wherein the evaluation unit is further configured to determine an inhaled dose per breath and a total inhaled dose per application based on the determined aerosol dose rate in the inhalation device.

9. An inhalation device for providing an aerosol stream to a patient, wherein the inhalation device comprises:

the sensor module for determining an aerosol dose rate of an aerosol stream of claim 1;

an aerosol generator configured to generate the aerosol stream; and a patient interface configured to provide the aerosol stream to the patient.

10. A method for determining an aerosol dose rate of an aerosol stream, wherein the aerosol stream is provided to a patient by an inhalation device, wherein the method comprises:

attaching the sensor module of claim 1 to the inhalation device, wherein the inhalation device is configured to provide the aerosol stream to a patient;

generating at least one first measurement signal depending on a concentration of the aerosol stream within the measurement volume comprised by the sensor module;

generating at least one second measurement signal depending on a flow of the aerosol stream through the measurement volume; and determining the aerosol dose rate in the inhalation device based on a contemporaneous determination of an aerosol concentration from the at least one first measurement signal and an inhalation flow from the at least one second measurement signal.

11. The method of claim 10, wherein the method further comprises:

determining an inhaled dose per breath by integrating the aerosol dose rate over a single inhalation step from an initial time to a final time.

12. The method of claim 11, wherein the method further comprises:

determining a total inhaled dose per application after having taken an n-th breath through the inhalation device by summing the inhaled doses per breath.

* * * * *